US00PP31795P2

(12) United States Plant Patent
Wood

(10) Patent No.: US PP31,795 P2
(45) Date of Patent: May 26, 2020

(54) ***TAXUS* PLANT NAMED 'SMNTHDC'**

(50) Latin Name: ***Taxus* x *media***
Varietal Denomination: SMNTHDC

(71) Applicant: Timothy D Wood, Spring Lake, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/350,983

(22) Filed: Feb. 7, 2019

(51) Int. Cl.
*A01H 7/00* (2006.01)

(52) U.S. Cl.
USPC ..... Plt./215

(58) Field of Classification Search
USPC ..... Plt./215
CPC ..... A01H 7/00
See application file for complete search history.

(56) References Cited

PUBLICATIONS

Spring Meadow Flowering Shrubs 2018-2019, retrieved on Oct. 8, 2019, retrieved at https://springmeadownursery.com/files/resource_files/2018-2019_SMN_Catalog 1-47.pdf cover page, pp. 1-9,17 and https://springmeadownursery.com/files/resource_files/2018-2019_SMN_Catalog_48-100.pdf, p. 85. (Year: 2019).*

* cited by examiner

*Primary Examiner* — June Hwu
(74) *Attorney, Agent, or Firm* — Cassandra Bright

(57) ABSTRACT

A new and distinct *Taxus* cultivar named 'SMNTHDC' is disclosed, characterized by upright growth, a compact branching habit, and fresh yellow-green and green foliage. The new cultivar is a *Taxus*, suitable for ornamental garden purposes.

1 Drawing Sheet

Latin name of the genus and species: *Taxus* x *media*.
Variety denomination: 'SMNTHDC'.

BACKGROUND OF THE INVENTION

The new cultivar is a product of a planned breeding program by the inventor to produce new forms of *Taxus* x *media*. This new variety, hereinafter referred to as 'SMNTHDC', was discovered and selected by the inventor Timothy Wood at a commercial nursery in Grand Haven, Mich. in 2006. The new variety is a result of an open pollination. The female parent is the unpatented variety *Taxus* x *media* 'Hicksii'; the pollen parent is unidentified.

After identifying the new variety as a potentially interesting selection, softwood cuttings were taken at the same nursery in Grand Haven, Mich. in 2011. The inventor continued controlled testing and propagation, assessing stability of the unique characteristics of this variety. At least seven generations have been reproduced and have shown that the unique features of this cultivar are stable and reproduced true to type. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'SMNTHDC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNTHDC' These characteristics in combination distinguish 'SMNTHDC' as a new and distinct *Taxus* cultivar:

1. Fresh yellow-green to green foliage color.
2. Distinctive narrow columnar plant shape.
3. Rapid growth.
4. Suitability for container cultivation.

COMPARISON TO PARENT VARIETY

'SMNTHDC' is similar in most horticultural characteristics to the parent variety. Plants of the new cultivar 'SMNTHDC' however, differ in the following:

1. New variety is more compact than the parent.
2. New variety is narrower than the parent.

COMMERCIAL COMPARISON

In addition to the seed parent, 'SMNTHDC' can be compared to the commercial variety *Taxus* x *media* 'Matinecock', unpatented. The varieties are similar in most horticultural characteristics, however, plants of 'SMNTHDC' differ in the following:

1. New cultivar is larger in diameter than this comparator.
2. New variety has lighter green foliage than this comparator.

BRIEF DESCRIPTION OF THE PHOTOGRAPH

The accompanying photograph illustrates in full color a typical plant of 'SMNTHDC' grown outdoors in Grand Haven, Mich. The plant is approximately 5 years old, and is shown in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNTHDC' plants grown outdoors in Grand Haven, Mich. Plants are approximately 2-3 years old, in a #3 size container. Measurements and numerical values represent averages of typical plant types.

Botanical classification: *Taxus* x *media* 'SMNTHDC'.

PROPAGATION

Time to rooting: 30 days at approximately 10° C.

Time to produce a rooted cutting: 3 months.

Root description: Fibrous, thick, dense, freely branched. White or tan in color, not accurately measured by R.H.S. chart.

PLANT

Growth habit: Upright.

Height: 68 cm.

Plant spread: 39 cm.

Growth rate: Rapid. Approximately 40-50 cm per year until mature height of about 300 cm.

Branching habit: Upright, compact.

Basal branching: None.

Pinching required: Some.

Stems:

- *Length*.—Average 15 to 18 cm.
- *Diameter*.—0.7 cm.
- *Color*.—New growth: RHS Green 143C. Mature growth: RHS Greyed-Orange 165A.
- *Appearance*.—Round.
- *Aspect/angle*.—0°.
- *Strength*.—Strong.
- *Pubescence*.—None.

Lateral branches:

- *Number*.—5.
- *Length*.—56 cm.
- *Diameter*.—8 mm.
- *Strength*.—Strong.

Internode length: 5 mm.

Trunk bark:

- *Color*.—Near RHS 200C.
- *Texture*.—Scaly, slightly peeling.

FOLIAGE

General description: Needle-like, imbricate, slightly appressed.

Leaf:

- *Arrangement*.—Alternate, single.
- *Shape of blade*.—Linear, needle-like.
- *Average length*.—2.5 cm.
- *Average width*.—2 mm.
- *Apex*.—Cuspidate.
- *Base*.—Oblique.
- *Margin*.—Entire.
- *Texture of top surface*.—Smooth.
- *Texture of bottom surface*.—Smooth.
- *Color*.—Young foliage upper side: RHS Yellow-Green 145A. Young foliage under side: RHS Yellow-Green 145A. Mature foliage upper side: Near RHS Green 138A. Mature foliage under side: RHS Yellow-Green 144A.
- *Venation*.—Linear, indistinguishable from leaf blade.

Petiole:

- *Length*.—2 mm.
- *Diameter*.—1 mm.
- *Texture, upper side*.—Smooth.
- *Texture, under side*.—Smooth.
- *Color, upper side*.—RHS Yellow-Green 144A.
- *Color, under side*.—RHS Yellow-Green 144A.

FLOWER

Flowering not observed.

OTHER CHARACTERISTICS

Fruit and seeds: Not observed.

Disease and pest resistance: Neither resistance nor susceptibility observed.

Drought tolerance: No tolerance for drought.

Temperature tolerance: USDA Zones 3-9.

What is claimed is:

1. A new and distinct cultivar of *Taxus* plant named 'SMNTHDC' as herein illustrated and described.

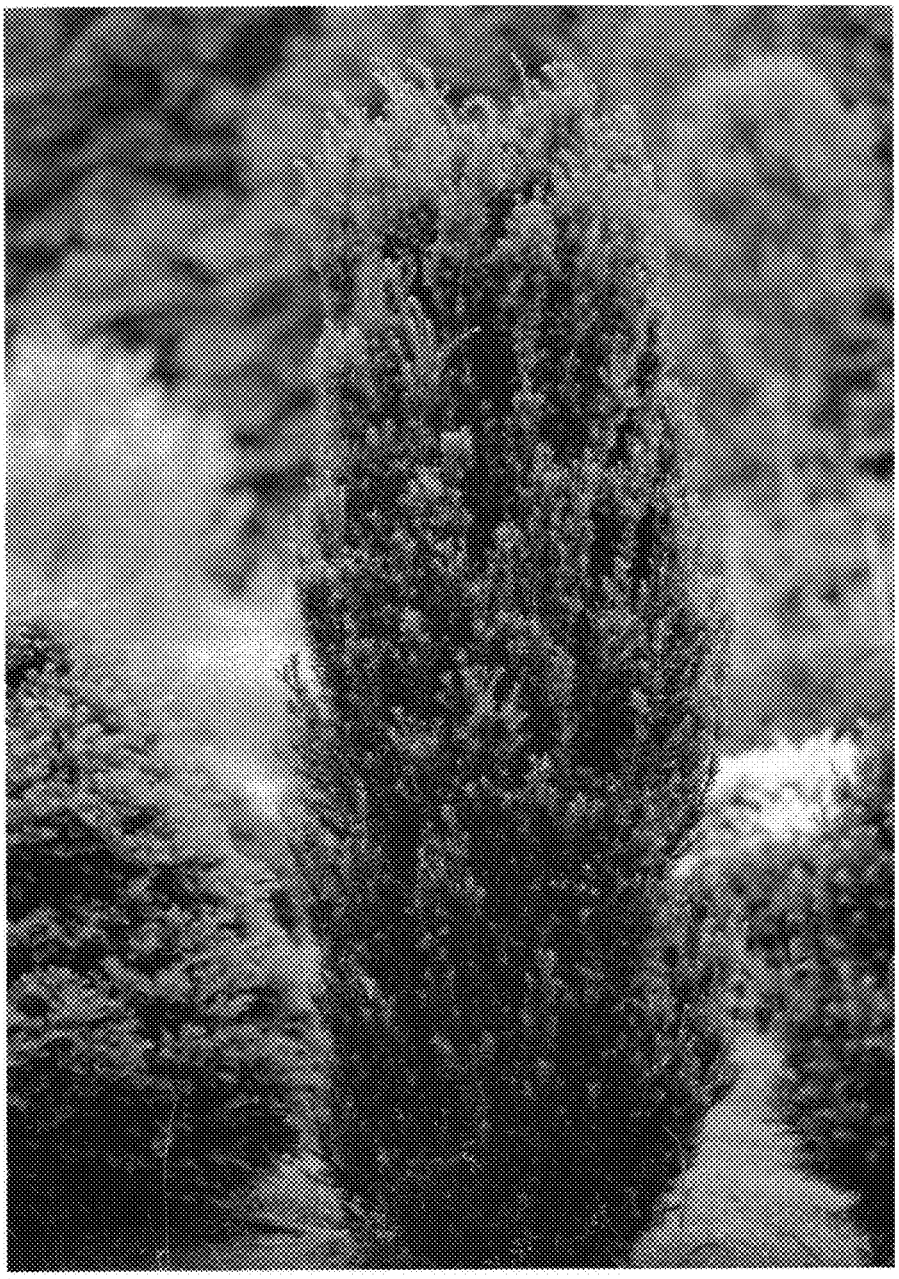

* * * * *